US00PP22907P2

(12) United States Plant Patent
Nielsen

(10) Patent No.: US PP22,907 P2
(45) Date of Patent: Jul. 31, 2012

(54) *DAHLIA* PLANT NAMED 'DANITTEN'

(50) Latin Name: ***Dahlia* Cav.**
Varietal Denomination: DANITTEN

(75) Inventor: Rune Harboe Nielsen, Groennegyden (DK)

(73) Assignee: Dalina ApS, Odense N (DK)

( * ) Notice: Subject to any disclaimer, the term of this patent is extended or adjusted under 35 U.S.C. 154(b) by 0 days.

(21) Appl. No.: 13/067,060

(22) Filed: May 5, 2011

(51) Int. Cl.
*A01H 5/00* (2006.01)

(52) U.S. Cl. ..... Plt./321

(58) Field of Classification Search ..... Plt./321
See application file for complete search history.

(56) References Cited

OTHER PUBLICATIONS

Printout of application information from Community Plant Variety Office (CPVO) website for corresponding CPVO application No. 2011/0689 filed Mar. 18, 2011 (1 page). (http://www.cpvoextranet.cpvo.europa.eu).

*Primary Examiner* — June Hwu
*Assistant Examiner* — Louanne Krawczewicz Myers
(74) *Attorney, Agent, or Firm* — Foley & Lardner LLP

(57) ABSTRACT

A new distinct cultivar of *Dahlia* plant named 'DANITTEN', characterized by its cylindrical upright shape, with stiff and strong lateral stems and thick (mostly compound) leaves with up to 5 leaflets; color of mature leaves RHS 147A (upper side), RHS 191A (Underside); compound leaves 8-20 cm in length, and 8-20 cm in width. The few single leaves, present near ground level, are 16-21 cm in length and 8-10 cm in width. Composite flower heads are 9-11 cm in diameter, with a large number of ray florets (about 110 to 130). The ray florets are green-yellow (RHS 1A) near base, transforming into yellow (RHS 12B) at apex.

8 Drawing Sheets

Latin name of the genus and species of the claimed plant: *Dahlia* Cav.
Variety denomination: 'DANITTEN'.

BACKGROUND OF THE INVENTION

The present invention relates to a new and distinct cultivar of *Dahlia* plant, botanically known as *Dahlia* Cav., of the Compositae (Asteraceae) family, hereinafter referred to by the cultivar name 'DANITTEN'.

The new *Dahlia* cultivar is a product of a planned breeding program conducted by the inventor, Rune Nielsen, in Stige, Denmark. The objective of the breeding program is to develop a new *Dahlia* cultivar with an upright, strong and healthy growth habit, suitable for large scale container production and with good garden performance; fully double flowers creating globular-shaped flower head (composite flower heads with many ray florets) with an attractive inflorescence color.

The new *Dahlia* cultivar originated from a cross, made in a controlled breeding program by the inventor in 2006, in Stige, Denmark. The female or seed parent is white *Dahlia* cultivar designated 'DASYTTEN' (patented, U.S. Plant Pat. No. 21,037). The male or pollen parent is a yellow-orange colored *Dahlia* variety designated 5213M (unpatented).

Asexual reproduction of the new *Dahlia* cultivar by terminal cuttings was first performed in November, 2007 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DANITTEN', which in combination distinguish this *Dahlia* as a new and distinct cultivar:

1. Cultivar with cylindrical upright shape;
2. Cultivar with stiff and strong lateral stems and thick, mostly compound leaves, with up to 5 leaflets. Color of mature leaves yellow-green (RHS 147A) (upper side), greyed-green (RHS 191A) (Underside);
3. Compound leaves 8-20 cm in length, and 8-20 cm in width. The few single leaves present near ground level are 16-21 cm in length and 8-10 cm in width;
4. Composite flower heads, 9-11 cm in diameter, with a large number of ray florets (about 110 to 130); and
5. Ray florets which are green-yellow (RHS 1A) near base, transforming into yellow (RHS 12B) at apex.

Plants of the new *Dahlia* 'DANITTEN' differ from plants of the parent, 'DASYTTEN' (patented, U.S. Plant Pat. No. 21,037) in the traits described in Table 1. (The unpatented male parent 5213M is no longer available for comparison).

TABLE 1

Comparison with Parent Variety

| Trait | New Cultivar 'DANITTEN' | Comparison Cultivar 'DASYTTEN' |
|---|---|---|
| Plant Size | | |
| Height: | About 35-45 cm. | About 45-50 cm. |
| Diameter: | About 40-45 cm. | About 35-40 em. |
| Overall Plant Shape: | Cylindrical, upright, with basal branching. Inflorescences in composite heads. | Cylindrical, upright to outward, with basal branching. Inflorescences in composite heads. |
| Basal branches | | |
| Length: | 8-16 cm. | 12-14 cm. |
| Diameter: | 8-12 mm | 6-11 mm |
| Strength: | Stiff and strong. | Stiff and strong. |

TABLE 1-continued

| Comparison with Parent Variety | | |
|---|---|---|
| Trait | New Cultivar 'DANITTEN' | Comparison Cultivar 'DASYTTEN' |
| Color: | RHS 146B (yellow-green). | Brown, RHS 200A on older stems, and yellow-green, RHS 147B, on younger stems or stems exposed to less light |
| Leaves | | |
| Colour mature upper side: | RHS 147A (yellow-green), | RHS N189A (greyed-green), |
| Underside: | RHS 191A (greyed-green). | RHS 191B (greyed-green). |
| Peduncle | | |
| Colour mature: | RHS 197A (greye-green) | RHS 200B (brown) |
| Colour immature: | RHS 146B (yellow-green) | RHS 146B (yellow-green) |
| Color of ray florets Upper Side: | RHS 1A (green-yellow) near base transforming into RHS 12B (yellow) at apex. | Near base RHS 1B (green-yellow), transitioning to RHS 17C (yellow-orange) at apex. |

Of the many commercial cultivars known to the present inventor, the most similar in comparison to the new *Dahlia* 'DANITTEN' is the *Dahlia* cultivar 'DASYTTEN', in the characteristics described in Table 2:

TABLE 2

| Comparison with Comparison Variety | | |
|---|---|---|
| Trait | New Cultivar 'DANITTEN' | Comparison Cultivar 'DASYTTEN' |
| Plant Size | | |
| Height: | About 35-45 cm | About 45-50 cm. |
| Diameter: | About 40-45 cm | About 35-40 cm. |
| Overall Plant: Shape | Cylindrical, upright, with basal branching. Influrescences in composite heads. | Cylindrical, upright to outward, with basal branching. Inflorescences in composite heads. |
| Basal branches | | |
| Length: | 8-16 cm. | 12-14 cm. |
| Diameter: | 8-12 mm | 6-11 mm |
| Strength: | Stiff and strong. | Stiff and strong. |
| Color: | RHS 146B (yellow-green), | Brown, RHS 200A on older stems, and yellow-green, RHS 147B, on younger stems or stems exposed to less light. |
| Leaves | | |
| Colour mature upper side: | RHS 147A (yellow-green), | RHS N189A (greyed-green), |
| Underside: | RHS 191A (greyed-green). | RHS 191B (greyed-green). |
| Peduncle | | |
| Colour mature: | RHS 197A (greyed-green) | RHS 200B (brown) |
| Colour immature: | RHS 146B (yellow-green) | RHS 146B (yellow-green) |
| Color of ray florets Upper side: | RHS 1A (green-yellow) near base transforming into RHS12B (yellow) at apex. | Near base RHS 1B (green-yellow) transitioning to RHS 17C (yellow-orange) at apex. |

BRIEF DESCRIPTION OF THE PHOTOGRAPHS

The accompanying photographs illustrate the overall appearance of the new *Dahlia* 'DANITTEN' showing the colors as true as is reasonably possible with colored reproductions of this type. Colors in the photographs may differ slightly from the color value cited in the detailed botanical description, which accurately describe the color of 'DANITTEN'.

DETAILED BOTANICAL DESCRIPTION

Figure 1:
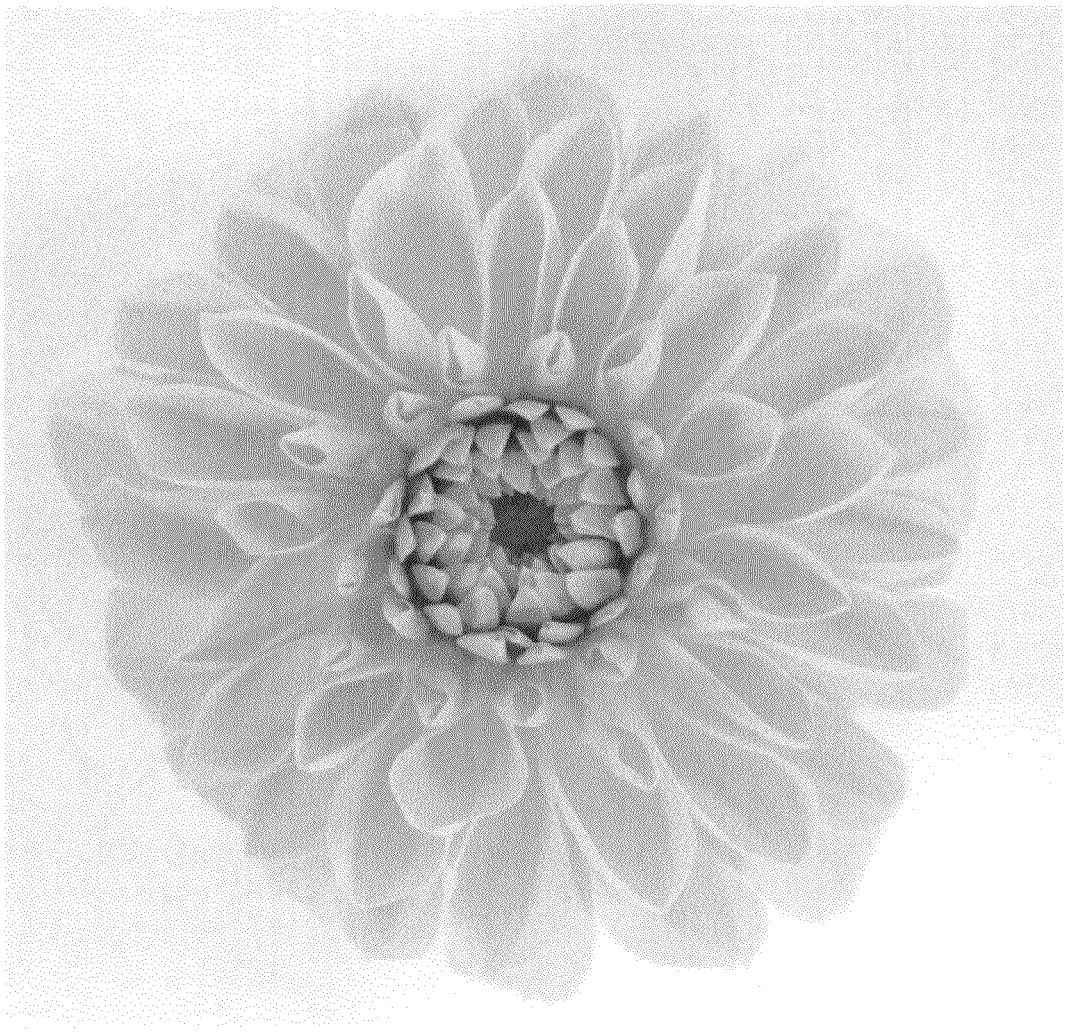
FIG. 1 shows a close-up view of the composite flower head from 'DANITTEN'.
Figure 2:
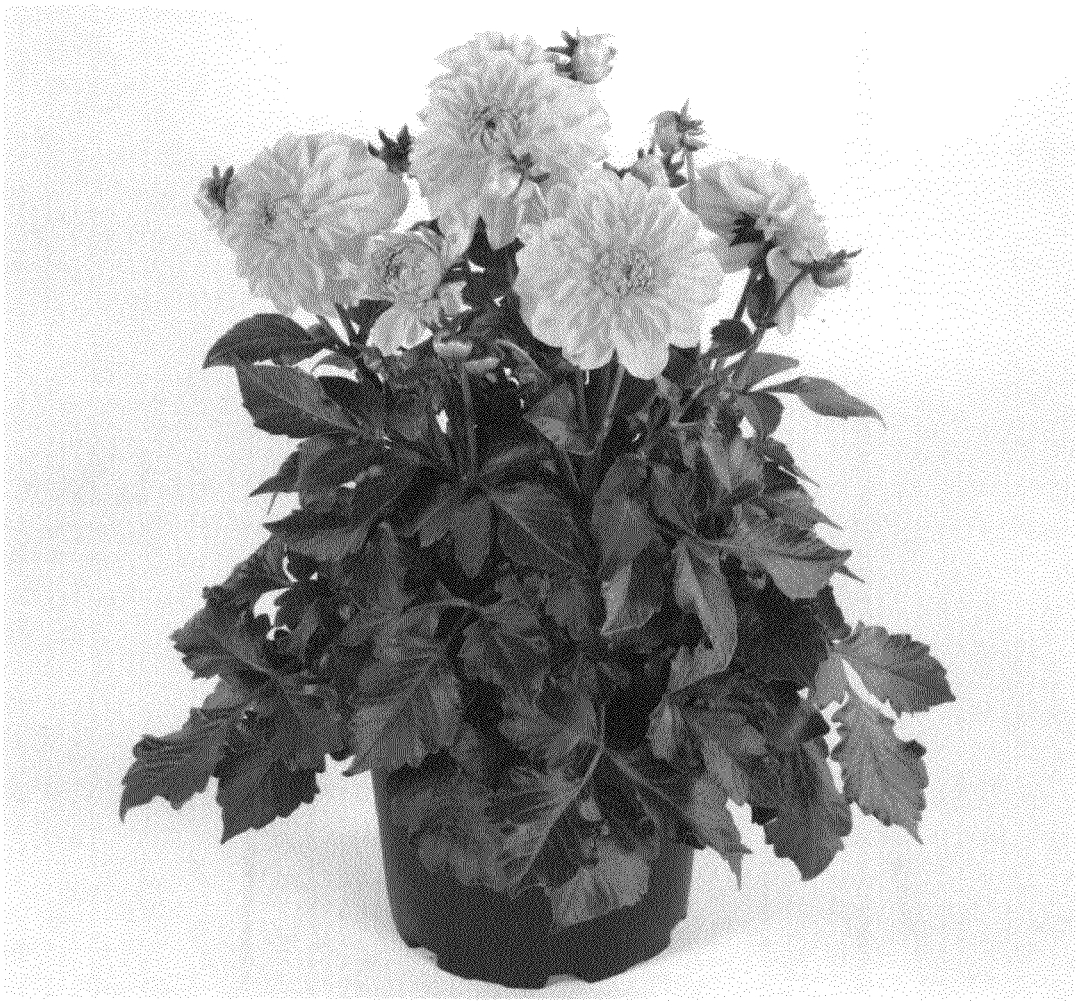
FIG. 2 shows a side view perspective of a typical flowering plant of 'DANITTEN' in a 19 cm pot, at 12 weeks of age after potting the young plant.
Figure 3:
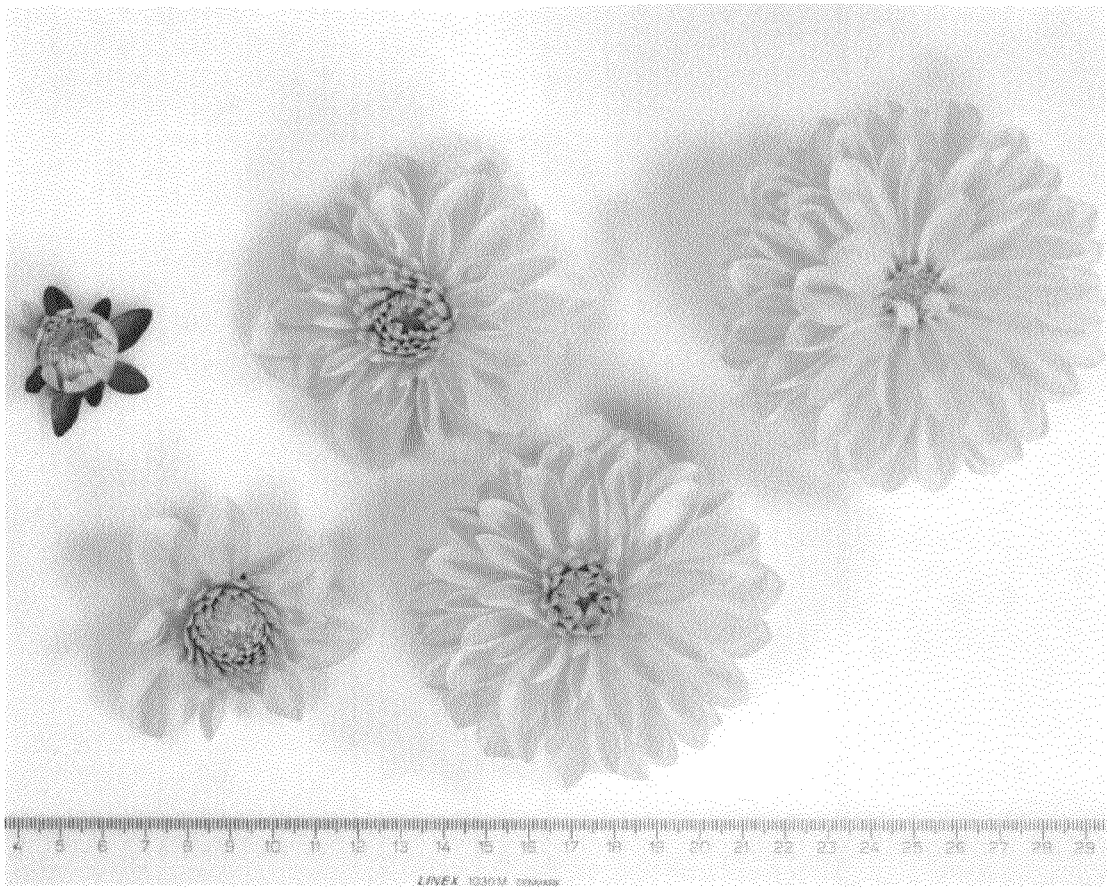
FIG. 3 shows a close-up view of different development stages of the composite flower head of 'DANITTEN' at (from left to right) first blooming, +2 days, +4 days, +6 days, and +10 days.
Figure 4:
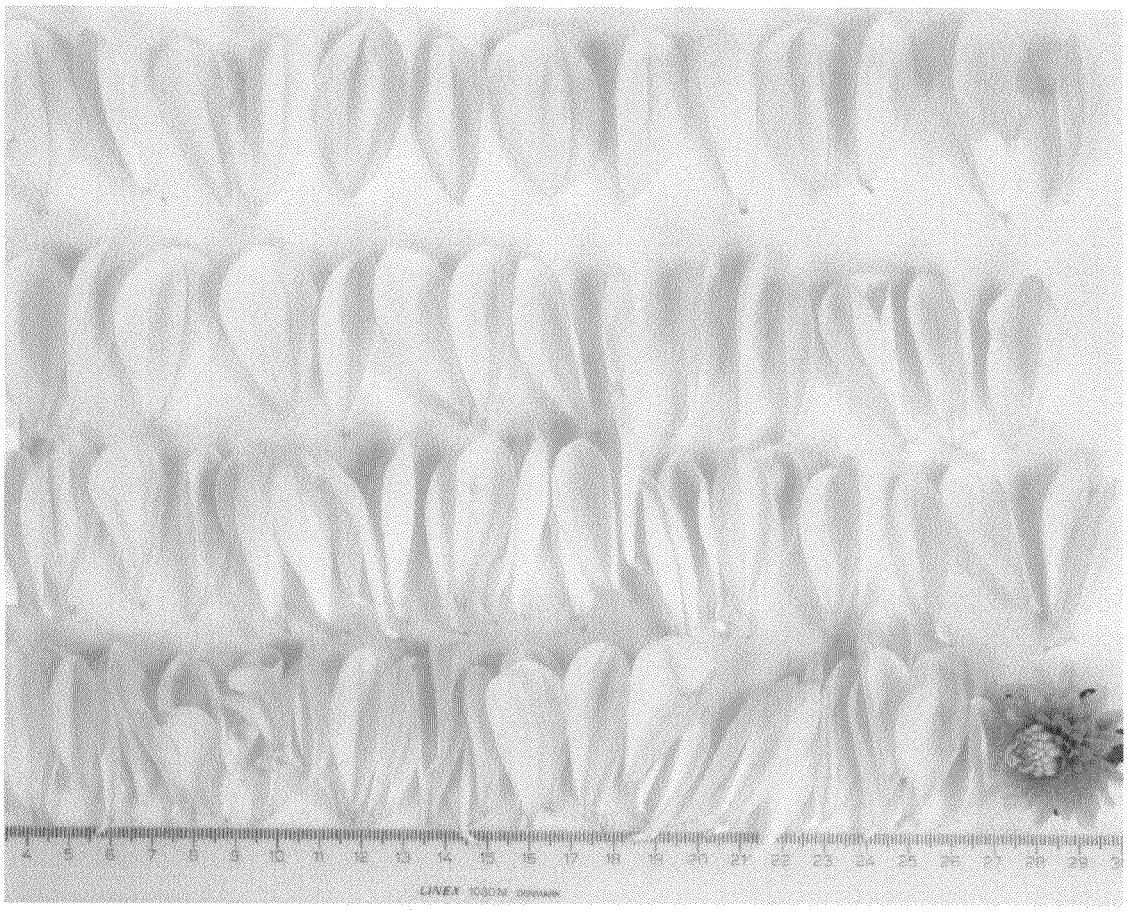
FIG. 4 shows a close-up view of the 120-140 ray florets from one composite flower head of 'DANITTEN'
Figure 5:
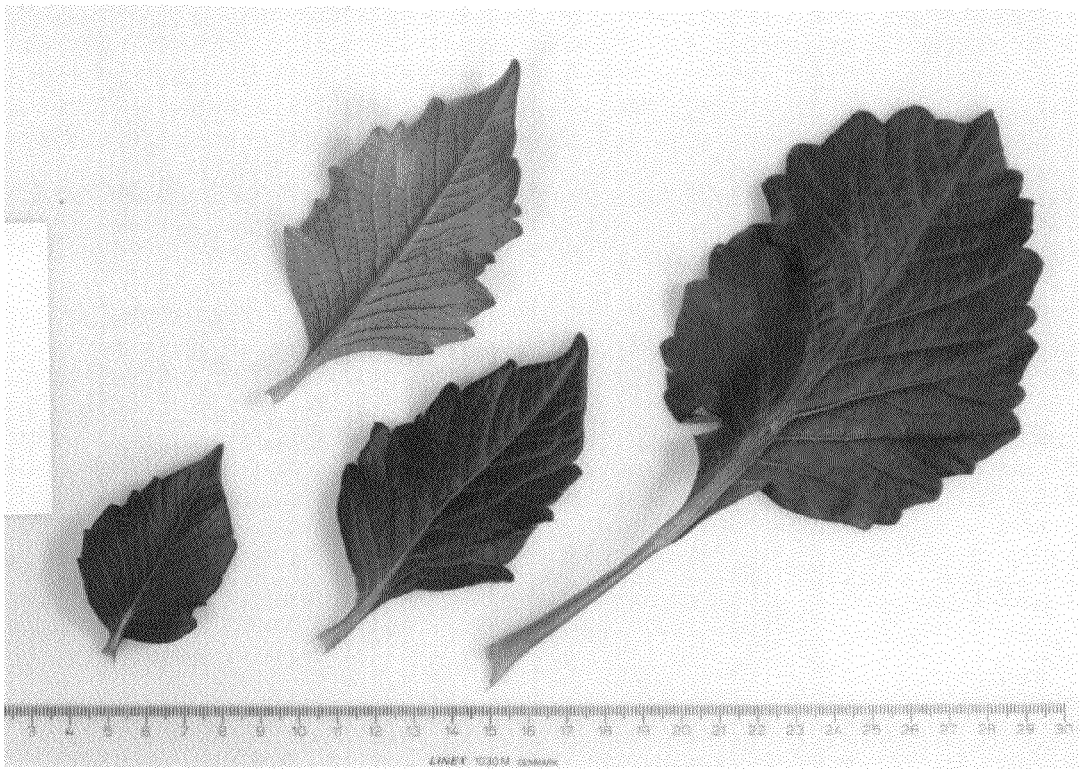
FIGS. 5, 6 and 7 shows a close-up view of the different single and compound leaf sizes of 'DANITTEN'.
Figure 6:
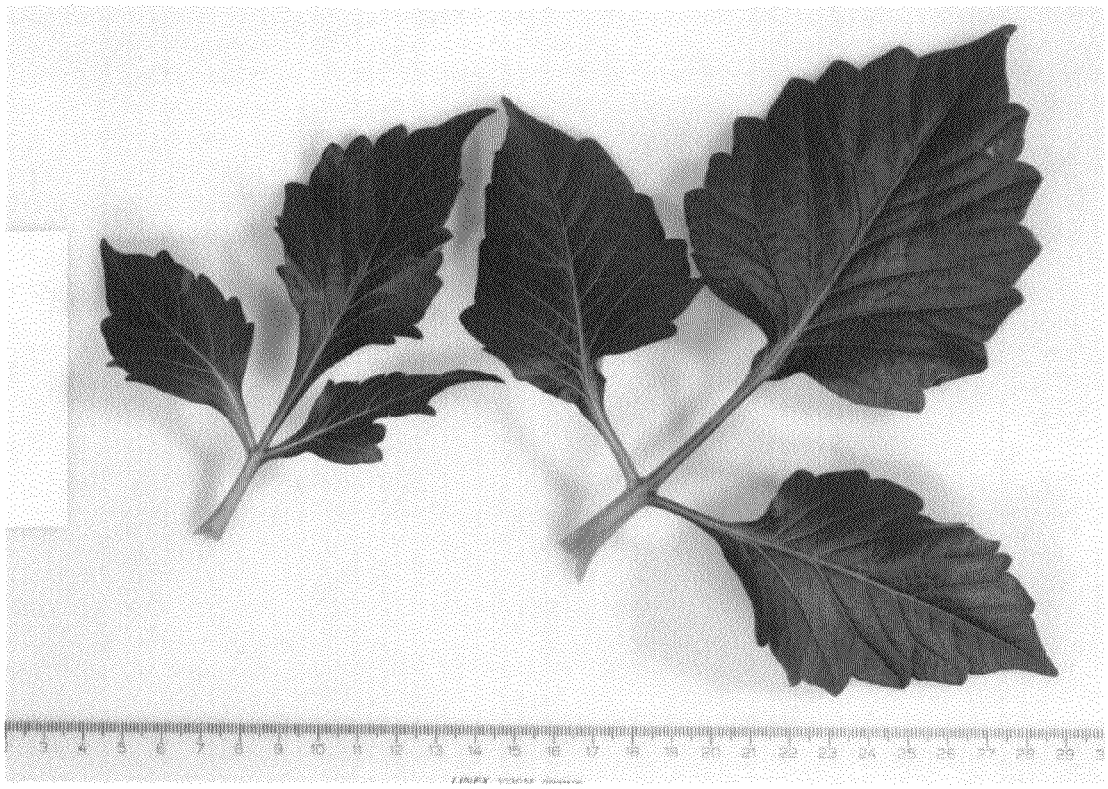
Figure 7:
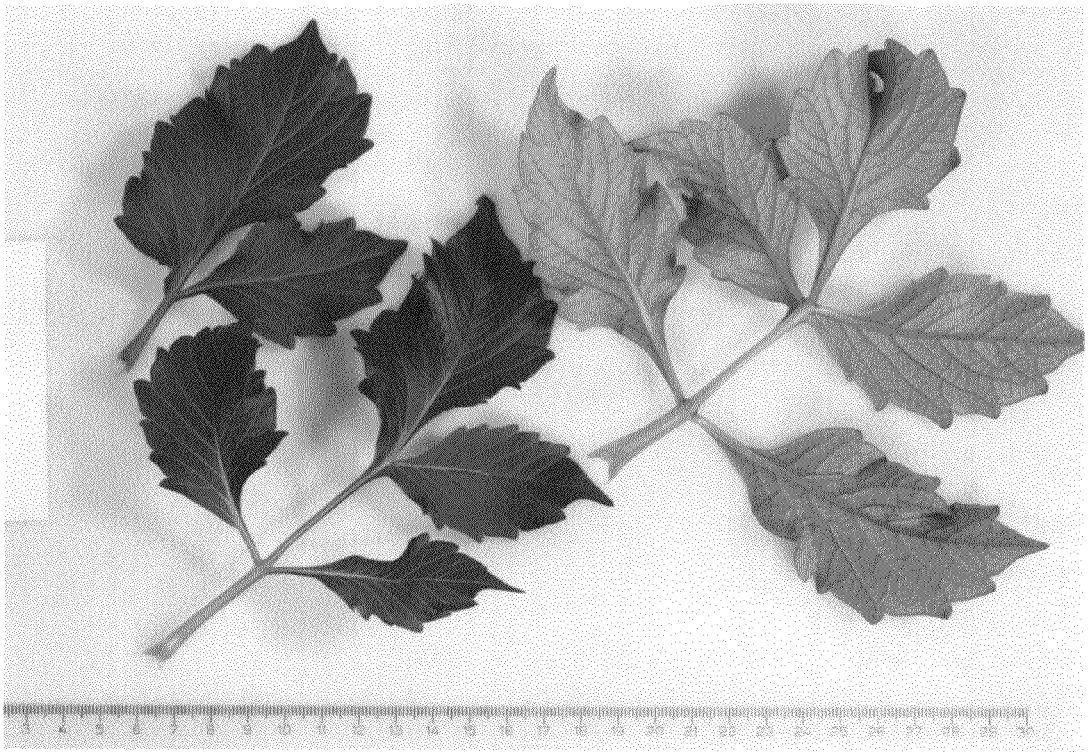
Figure 8:
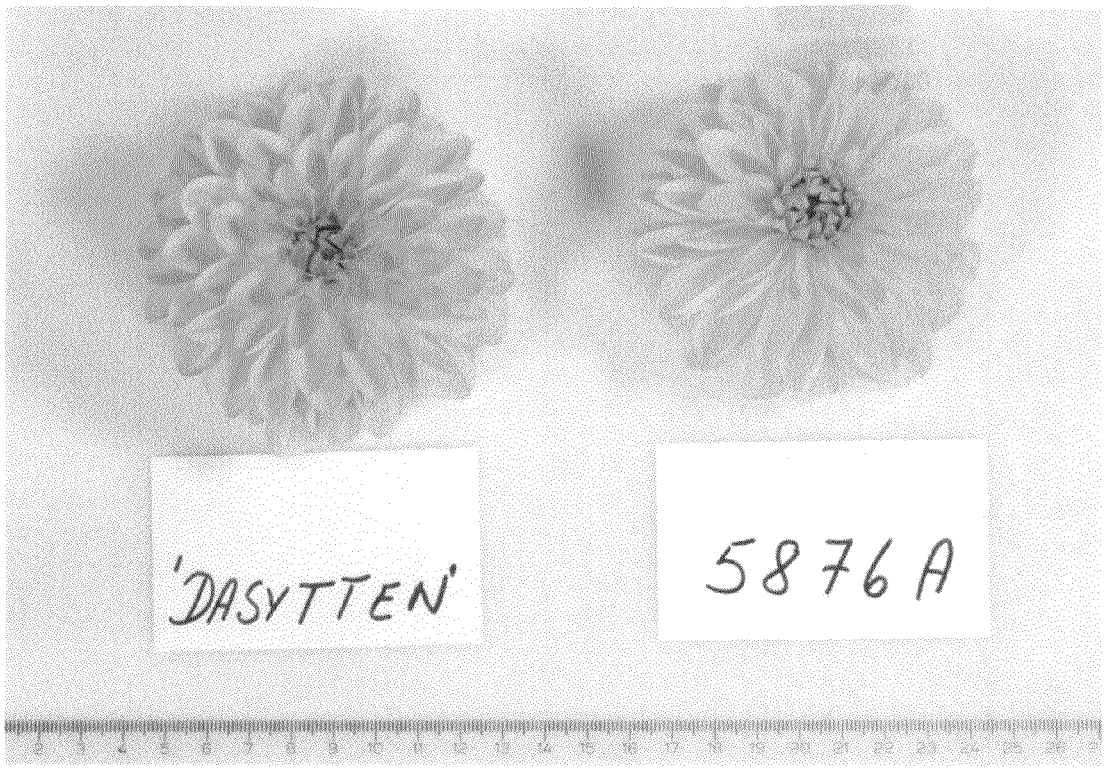
FIG. 8 shows a comparison between 'DASYTTEN' and 'DANITTEN', (Breeders reference: 5876A).

The new *Dahlia* 'DANITTEN' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dahlia* 'DANITTEN' as grown in a protected environment in a glass, greenhouse in Fyn, Odense, Denmark, under conditions which closely approximate those generally used in commercial practice. During propagation, conducted in a glasshouse, vegetative cuttings were planted in small propagation pots with peat as substrate, and then placed in a plastic tunnel averaging about 21° C. and received photoperiodic treatments of 18 hours. Supplementary light was given when natural light fell below 3000-4000 Lux. Rooting occurred about 12 days after planting. In third week after planting the cutting, young plants were potted in an 19 cm pot in a glass covered greenhouse, maintained at 18° C. to 22° C. during the day, and at 17° C. to 19° C. during the night. Photoperiodic treatments were continued at 18 hours, and supplementary light was given when natural light fell below 3000-4000 Lux. Irrigation was done with water. The EC measured in the soil was maintained between 2.0 to 3.0 mS/m. One week after potting, the first growth regulation was given: a spray with 85% daminozide, 0.2%, 40-100 m1/m2. During the production time, 9 additional sprayings were given with 85% daminozide, 0.2%, 40-100 m1/m2.

Color references are made to The Royal Horticultural Society Colour Chart (RHS), 2001 edition, except where general colors of ordinary significance are used. Color values were taken under March daylight conditions at approximately 12:00 PM and 2:00 PM in Fyn, Odense, Denmark. The age of the 'DANITTEN' plants described is 15 weeks (including propagation time).

Classification:

*Botanical.—Dahlia* Cav.

Parentage:

*Female or seed parent.—Dahlia* variety designated DASYTTEN (patented, U.S. Plant Pat. No. 21,037).

*Male or pollen parent.—Dehlia* variety designated 5213M (Unpatented).

Propagation:

*Type*.—Vegetative terminate cuttings.

*Time and temperature to initiate roots*.—About 9 to 12 days at 21° C. in tunnels or flat covered in a greenhouse.

*Time and temperature to produce a rooted young plant*.—About 28 days at 21° C. during rooting phase, followed by 18° C.

*Rooting habit*.—Fine, fibrous; Color of root: RHS Yellow-white 158C.

*Tuber development*.—Plants might develop tubers in late fall when planted outside.

Plant description:

*General appearance and form*.—Cylindrical, upright, with basal branching. Inflorescences in composite heads.

*Growth rate*.—Growing about 3 to 6 cm per week during production period.

*Plant height* (*from soil level to top of plant plane*).—About 35 cm to 45 cm.

*Plant width* (*spread*).—About 40 cm to 45 cm.

*Crop time to produce a mature flowering plant*.—It requires 3 to 4 weeks to produce a young plant in a 35 mm propagation plug. After potting 9 to 12 weeks are required to produce finished flowering plants in 19 cm pots.

Stem:

*Shape*.—Round.

*Length*.—About 8 cm to 16 cm.

*Diameter*.—About 10 mm to 14 mm.

*Strength*.—Stiff and strong.

*Aspect*.—Upright to slightly outward.

*Texture*.—Smooth and glabrous.

*Color*.—Mature: RHS 146B. Immature: RHS 146B.

Branches:

*Branching habit*.—Basal branching with lateral branches.

*Number of basal branches per plant*.—About 3-5 (when pinched above 3 pair of leaves).

*Length* (*including flowers*).—About 8 cm to 18 cm.

*Diameter*.—About 10 mm to 14 mm.

*Strength*.—Stiff and strong.

*Aspect*.—Upright to slightly spreading.

*Texture*.—Smooth and glabrous.

*Color*.—Mature: RHS 146B. Immature: RHS 146B.

*Internodes length*.—About 25 to 55 mm.

*Internodes color*.—RHS 146B.

Foliage description:

*Type*.—Lower leaves: Compound, 3 lobed and a few single. Middle leaves: Compound, 5 lobed. Upper leaves: Compound, 2-3 lobed and a few single.

*Number of leaves per branch*.—About 8 to 12 per branch.

*Color of leaves* (*leaves and leaflets*).—Color of upper side (mature) RHS 147A. Color of underside (mature) RHS 191A. Color of upper side (immature) RHS 137A. Color of underside (immature) RHS 137C.

*Venation* (*leaves and leaflets*).—Pattern: Pinnate. Color of upper side: RHS 146A. Color of underside: RHS 146C.

Compound leaves:

*Number of leaflets per compound leaf*.—3 to 5.

*Length of compound leaf*.—8 cm to 20 cm.

*Width of compound leaf*.—8 cm to 20 cm.

*Petiole of compound leaves*.—Shape: Semi circular, with deep furrow on adaxial side. Length: 1.5 cm to 6 cm. Diameter: 3 mm to 10 mm. Texture: Smooth and glabrous. Color: RHS 146B.

*Leaflets of compound leaf*.—Terminal leaflet quantity: 1. Terminal leaflet length: 5 cm to 10 cm. Terminal leaflet width: 4 cm to 9 cm. Terminal leaflet shape: Ovate. Terminal leaflet shape at apex: Acuminate. Terminal leaflet shape at base: Cordate to rounded (not always symmetric). Terminal leaflet margin: Dentate. Terminal leaflet texture (both sides): Rugose. Rachis length: 1 cm to 4 cm. Rachis Diameter: 2 mm to 4 mm. Rachis color: RHS 146B. Lateral leaflet quantity: 2 to 4. Lateral leaflet length: 4 cm to 11 cm. Lateral leaflet width: 3 cm to 7 cm. Lateral leaflet overall shape: Ovate. Lateral leaflet shape at apex: Acuminate (mostly asymmetric). Lateral leaflet shape at base: Rounded (not always symmetric). Lateral leaflet margin: Dentate. Lateral leaflet texture (both sides): Rugose.

Simple leaves:

*Simple leaves overall shape*.—Ovate.

*Simple leaves shape at apex*.—Acuminate.

*Simple leaves shape at base*.—Cordate to rounded.

*Simple leaves length*.—8 cm to 21 cm.

*Simple leaves width*.—5 cm to 10 cm.

*Simple leaves margin*.—Dentate.

*Simple leaves texture*.—Rugose.

*Petiole shape*.—Semi circular, with deep furrow on adaxial side.

*Petiole length*.—1 cm to 7 cm.

*Petiole diameter*.—3 mm to 10 mm.

*Petiole texture*.—Smooth and glabrous.

*Petiole color*.—RHS 146B.

Inflorescence description:

*Natural flowering season*.—Grown outside as a bedding plant, flowering occurs continuously during growing season from spring to autumn/(In Denmark, from June to beginning of October). Plants can be brought to flower anytime when grown under the recommended greenhouse conditions.

*Time to flower*.—60 to 80 days from potting a young plant until flowering.

*Inflorescence longevity on the plant*.—Inflorescence will maintain good color and substance for about 6-10 days; however, the longevity of individual inflorescence is highly dependent on temperature and light conditions. Inflorescence persistent.

*Type*.—Composite flower heads.

*Arrangement and shape*.—Persistent, single, composite inflorescences from leaf axils. Disc and ray florets arranged acropetally in a composite flower head. Upright, slightly spreading. Terminal young flower head/buds initially 0-30°. Buds from axillary shoots 60-100°. When flower opens 0-45°.

*Quantity of inflorescences heads*.—Freely flowering; about 14 buds and open inflorescences per plant.

*Fragrance*.—Soft honey.

*Bud* (*inflorescences head*).—Rate of opening (from showing color to fully open): 4 to 10 days. The rate of opening is highly dependent on temperature and light conditions. Length: About 10-14 mm. Diameter: About 16-22 mm. Shape: Flat globular. Texture: Glabrous, shining. Color: RHS 144A developing into RHS 144B.

*Peduncle*.—From both terminate and axillary shoots. Length: About 8-16 cm. Diameter: About 4-6 mm. Angle: About 0-20° from vertical. Strength: Stiff and strong. Texture: Glabrous. Color (mature): RHS 197A. Color (immature): RHS 146B.

*Receptacle*.—Height: 10-14 mm. Diameter: 12-14 mm. Color: RHS Yellow-Green 146A.

*Inflorescence head*.—Depth (height): 6-8 cm. Diameter: 9-11 cm. Disc diameter: 12-14 mm.

*Ray florets*.—Arrangement: Imbricate, in about 9 to 14 whorls of ray florets, each with 9 to 11 florets to equal a total of about 110-130 ray florets per flower head, depending on light and temperature conditions. Quantity per inflorescence head: 110-130. Length: 40-45 mm. Widths: 22-30 mm. Overall shape: Obovate. Apex shape: Obtuse. Base shape: Acuminate, slightly fused. Margin: Entire. Texture: Glabrous (upper side and underside). Colour when opening fused ray floret starting to show color: RHS 15A. Colour when fully opened Color upper side: RHS 1A near base, transforming into RHS 12B at apex. Color underside: RHS 1A near base transforming into RHS 12B at apex (less intense than the upper side).

*Disc florets*.—Arrangement: 30-40 yellow-orange disc florets arranged in center of inflorescence head. Appearance: Quantity per Inflorescence head: 35-45. Length: 15-17 mm. Diameter: 3 mm. Overall shape: Tubular. Apex shape: Star with 5 triangular tips. Base shape: Fused to tube. Color RHS 17B, RHS 145C near base.

*Phyllary*.—Arrangement: One subtending each floret. Quantity: 110-130. Length: 12-22 mm. Width: 6-9 mm. Overall shape: Rounded. Shape at apex: Acute with rounded tip. Shape at base: Fused. Margin: Entire. Color: Mature: RHS 151B on upper side. RHS 146A on underside of the 8-10 phyllaries in the outer whorl. Immature: RHS 151B (both sides).

*Bracts*.—Arrangement and appearance: Reflexed, involucral bracts. Quantity: 7-8. Length: 13-21 mm. Width: 7-10 mm. Overall shape: Subulate. Apex shape: Acute. Base shape: Sessile. Margin: Entire. Texture: Glabrous. Color mature Upper side: RHS 137A. Underside: RHS 137B. Colour immature Upper side: RHS 137A. Underside: RHS 137B.

Reproductive organs:

*Androecium*.—Location: Disc florets only. Stamen number: 5, fused into synandrous tube around style. Stamen length: About 6-10 mm. Anther shape: Tubular. Anther length: About 5-6 mm. Pollen amount: A lot. Pollen color: RHS N25C.

*Gynoecium*.—Location: Ray and disc florets (Gynoecium at ray florets is poorly developed). Quantity: 1. Pistil length: 15-17 mm. Stigma shape: Bifurcate. Stigma length: About 4 mm. Stigma color: Not visible due to the cover of pollen brushed of the anthers. It then appears RHS N25C. Style length: About 6 mm. Style color: RHS 151C. Ovary color: RHS 151C.

Seed/fruit: Seed and fruit production has not been observed.

Disease/pest resistance: Resistance to pathogens and pests common to *Dahlia* has not been observed.

Disease/pest susceptibility: Susceptibility to pathogens and pests common to *Dahlia* has not been observed.

Temperature tolerance: Plants of the new *Dahlia* have exhibited good tolerance to rain, wind and drought; however, flowering may cease during hot periods (temperatures above 25° C. ). Low temperature tolerance to 1° C.

Growth regulators: Daminozide (85% water soluble dry concentrate formulation).

What is claimed is:

1. A new and distinct cultivar of *Dahlia* plant named 'DANITTEN', as illustrated and described herein.

* * * * *